United States Patent [19]

Douthart et al.

[11] Patent Number: 5,514,256
[45] Date of Patent: May 7, 1996

[54] APPARATUS FOR IMPROVED DNA SEQUENCING

[75] Inventors: Richard J. Douthart, Richland; Shannon L. Crowell, Eltopia, both of Wash.

[73] Assignee: Battelle Memorial Institute, Richland, Wash.

[21] Appl. No.: 330,876

[22] Filed: Oct. 28, 1994

[51] Int. Cl.$^6$ .......................... G01N 27/26; G01N 27/447
[52] U.S. Cl. .......................... 204/464; 204/466; 204/614; 204/616
[58] Field of Search ............................. 204/299 R, 182.8, 204/301

[56] References Cited

U.S. PATENT DOCUMENTS

| | | | |
|---|---|---|---|
| 3,497,441 | 2/1970 | Paksi | 204/182.8 |
| 4,631,122 | 12/1986 | Pohl | 204/299 R |
| 5,234,559 | 8/1993 | Collier et al. | 204/182.8 |
| 5,306,403 | 4/1994 | Vo-Dinh | 204/182.8 |

OTHER PUBLICATIONS

Direct Transfer Electrophoresis Used for DNA Sequencing, by Fritz M. Pohl and Stephan Beck, *Methods in Enzymology*, vol. 155, p. 250, No month available 1987.

Ultrathin–layer isoelectric focusing in 50–100 μm polyacrylamide gels on silanized glass plates or polyester film, by Bertold J. Radola, Verlag Chemic. GmbH D–6940 Wienheim, No month available 1980, *Electrophoresis 1980*, pp. 43–56.

Rapid DNA sequencing by horizontal ultrathin gel electrophoresis, by Robert L. Brumley, Jr. and Lloyd Smith, *Nucleic Acids Research*, vol. 19, No. 15, pp. 4121–4126 No date available.

High speed DNA sequencing by capillary electrophoresis, Luckey, J. A., H. Drossman, A. J. Kostichka, D. A. Mead, J. D'Cunha, T. B. Norris, and L. M. Smith. No month available 1990, *Nucleic Acids Research*, vol. 18, No. 15 pp. 4417–4421.

Capillary gel electrophoresis for rapid, high resolution DAn sequencing, by Harold Swerdlow, and Raymond Gesteland, 1990, *Nucleic Acids Research*, vol. 18, No. 15 pp. 1415–1419.

High speed on–line DNA sequencing on ultrathin slab gels, by Stegemann, J., Schwager, C., Erfle, H., Hewitt, N., Voss, H., Zimmermann, J., and Ansorge, W. No month available 1991, *Nucleic Acids Research*, vol. 19, No. 3, pp. 675–676.

Applications of Dioxetane Chemiluminescent Probes to Molecular Biology, by Stephan Beck and Hubert Koster, *Analytical Chemistry*, Nov. 1990, 62, pp. 2258–2270.

DNA Sequencing Separations in Capillary Gels on a Modified Commercial DNA Sequencing Instrument, by Robert J. Zagursky and Randy M. McCormick, *Bio Techniques*, vol. 9, No. 1, No month available 1990, pp. 74–79.

Multiplex DNA Sequencing, by George M. Church and Stephen Kieffer–Higgins, *Science*, 8 Apr. 1988, pp. 185–187.

*Primary Examiner*—John Niebling
*Assistant Examiner*—John S. Starsiak, Jr.
*Attorney, Agent, or Firm*—Johnnie R. Hynson

[57] ABSTRACT

This invention is a means for the rapid sequencing of DNA samples. More specifically, it consists of a new design direct blotting electrophoresis unit. The DNA sequence is deposited on a membrane attached to a rotating drum. Initial data compaction is facilitated by the use of a machined multi-channeled plate called a ribbon channel plate. Each channel is an isolated mini gel system much like a gel filled capillary. The system as a whole, however, is in a slab gel like format with the advantages of uniformity and easy reusability. The system can be used in different embodiments. The drum system is unique in that after deposition the drum rotates the deposited DNA into a large non-buffer open space where processing and detection can occur. The drum can also be removed in toto to special workstations for downstream processing, multiplexing and detection.

16 Claims, 12 Drawing Sheets

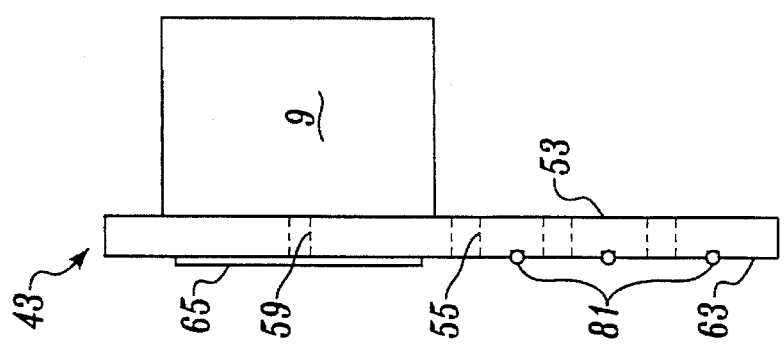
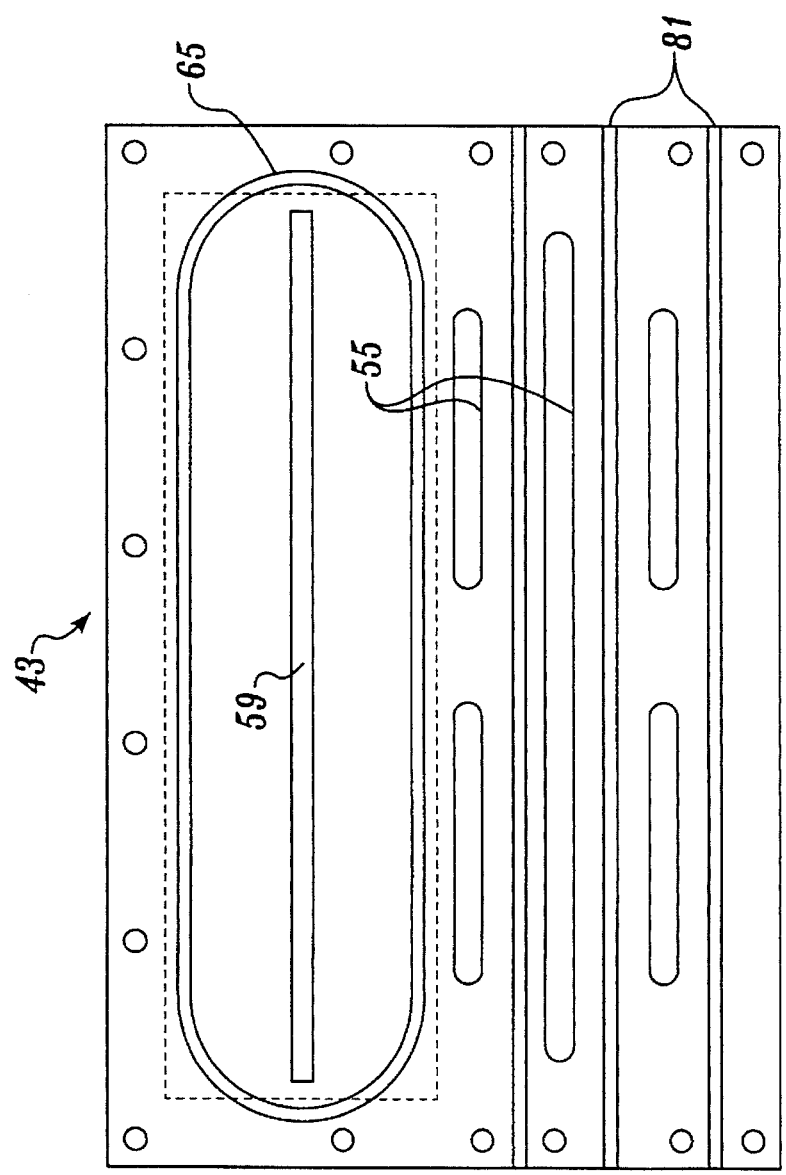
FIG. 5B.
FIG. 5A.

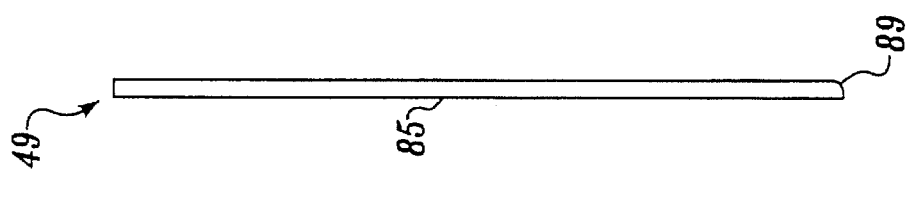
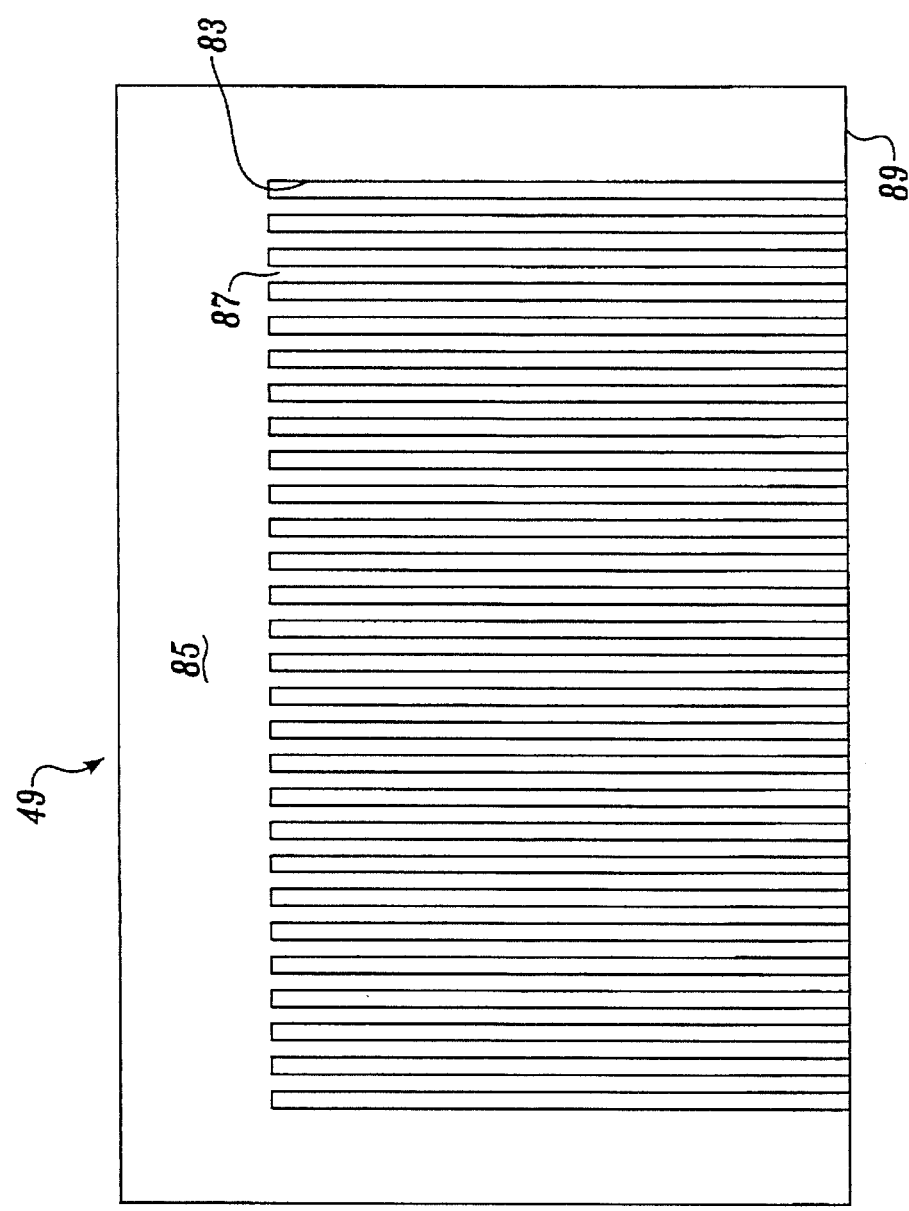
FIG. 7A.
FIG. 7B.

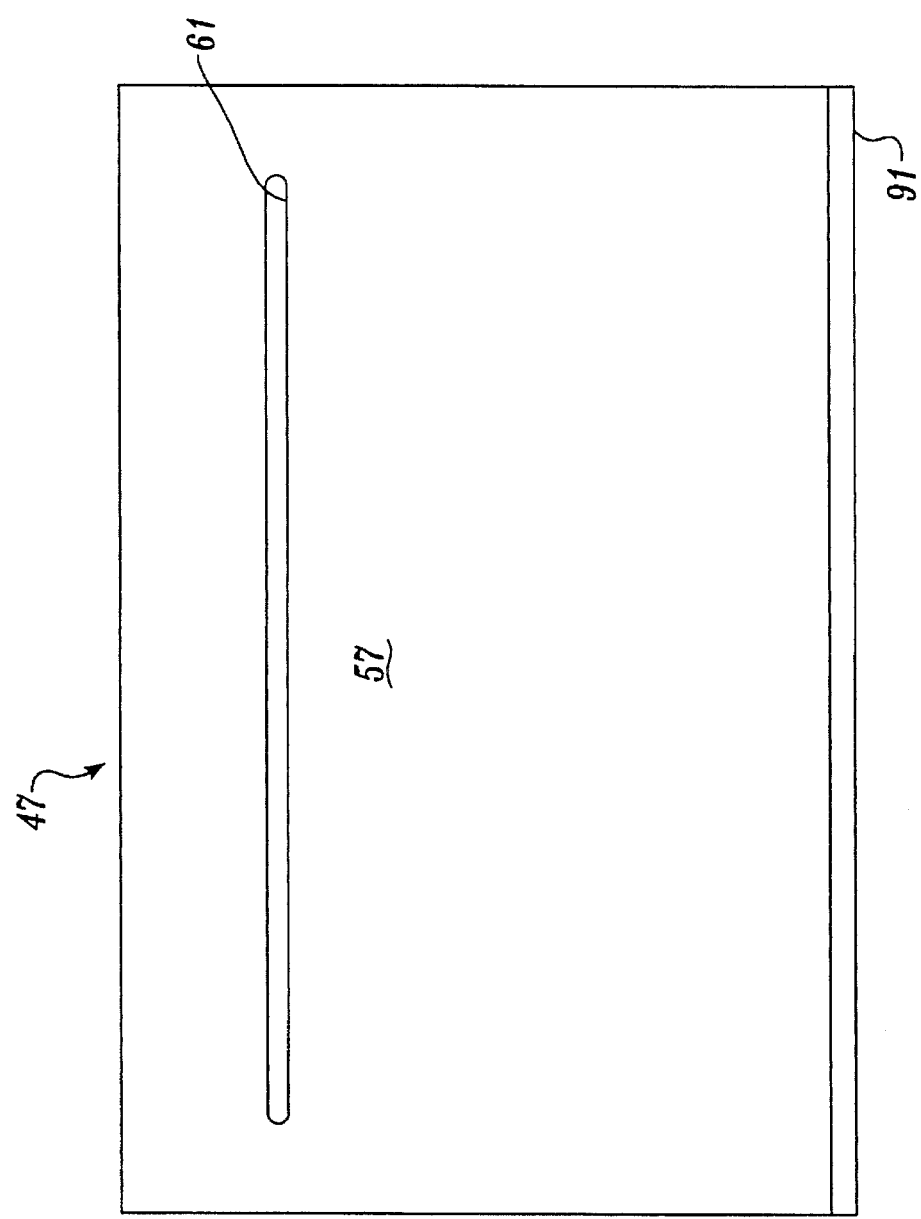

2

APPARATUS FOR IMPROVED DNA SEQUENCING

This invention was made with Government support under Contract DE-AC06-76RLO 1830 awarded by the U.S. Department of Energy. The Government has certain rights to the invention.

FIELD OF THE INVENTION

The instant invention relates generally to an apparatus and method for the rapid sequencing of DNA samples. More specifically, it is a means to reduce the time of sample analysis, to increase data compaction (the amount of data obtained per run), and to stabilize and facilitate downstream processing and detection in procedures involving hybridization techniques such as multiplexing. The invention although described for DNA sequencing is applicable to any procedure involving DNA electrophoretic separation and hybridization including DNA fingerprinting and restriction enzyme mapping.

BACKGROUND OF THE INVENTION

Over 40 million bases of genetic code originating from various organisms from humans to virus have been elucidated in the laboratory over the last decade. One of the objectives of the Human Genome Project is to sequence the approximately 3 billion bases that make up the human genome. Obviously, significant advances need to be made in DNA sequencing technology if this goal is ever to be achieved in a reasonable time.

The standard electrophoresis method is separation through a continuous polyacrylamide slab gel. In the preparation of a gel slab the liquid polyacrylamide gel is poured as a single continuous sheet between two glass plates separated by spacers at the boundaries. When the gel polymerizes a glass plate-gel-glass plate sandwich is formed. Sample loading slots are cast in the gel using a plastic comb shaped device set in place before the gel polymerizes and removed before loading the samples. This format is limited in the degree of data compaction that can be achieved in one run due to difficulties in lateral stability (sample drift) that occurs if the sample wells are placed any closer than 0.2 mm to one another and are any smaller than 4.0 mm in width. As a consequence of this limitation, improvements in slab technology have centered around decreases in running time and increases in the degree of resolution rather than increases in data compaction. The most significant advancement in this direction is the development of ultra-thin slab gels using extremely thin spacers that increase resolution and decrease running times.

A technology that does not appear to be limited by data compaction considerations is the recent development of gel-filled capillaries. Each capillary is an isolated electrophoresis unit that accepts a single sample and is limited theoretically only by the dimensions of the capillary. The large surface to volume ratio of the capillary allows highly efficient dissipation of electro-resistant generated heat. The greater the de-coupling of gel temperature from electroresistive generated energy the greater the effective field strength that can be applied. The linear range over which migration rate varies directly with field strength is extended using gel filled capillaries allowing separations at higher fields with greatly reduced running times.

The advantage in a single capillary, however, must somehow be translated to a large array of coupled capillaries each with the same characteristics which can be electrophoresed together under identical conditions to make this technology viable for DNA sequencing and to achieve significant data compaction. The creation of such an ensemble is a complex technical challenge that limits the usefulness of gel filled capillaries in real sequencing applications.

The ribbon channel plate of the instant invention has both the data compaction and energy dissipation characteristics of gel filled capillaries and the ease of preparation, reliability, and easy recasting characteristics of slab gels.

Current DNA sequencing chemistries establish the sequence of nucleotides (bases) along a DNA molecule by subjecting four sets of identical molecules that have been referenced chemically from the same point on the same end to a series of reactions. In one tube is an A (Adenine) specific, in one a T (Thymidine) specific, in one a G (Guanine) specific and in one a C (Cytosine) specific reaction. In each tube a set of molecular fragments is formed with each nucleotide position as terminator to a portion of the population. These reaction mixtures are then simultaneously electrophoresed through a gel where the populations separate into distinct bands of identical size fragments migrating inversely to their size (molecular weight) with the smaller fragments bands moving at faster rates than the larger ones. The set of resolved bands is called the sequence ladder. In the standard procedure, each of four sample wells formed in the gel when it sets up, is loaded with one of the nucleotide specific reaction mixtures. Upon simultaneous electrophoresis bands will form of size determined by the dimensions of the gel sample wells and will migrate in the order of the DNA sequence.

These fragment bands that make up the ladders can be labeled before separation with either radioactive or florescence labels. Another technique is to label each of the four types of nucleotide termination with a specific florescent molecule. Since the emission spectra of each label is different, a mixture of all four reactions can be electrophoresed from the same well in the gel effectively increasing data compaction four fold. In other techniques the resolved bands can be elucidated by hybridizing electro-eluted fragments on deposition membranes to specific labeled DNA fragment probes.

Labeled DNA probes can be hybridized to the sequence ladder, washed off, and then the ladder probed again. This recursive probe hybridization procedure is the basis for the Church multiplexing technique in which the data compaction can be increased up to 40 fold. In multiplexing, up to 40 different DNA samples of different sequence are mixed together prior to performing the DNA sequencing reactions. These samples are then processed together as if they were one. At the end of the procedure, the individual ladders associated with a particular sequence are revealed by hybridization with a labeled DNA probe specific for that sequence. The probe is then washed off and a new probe is applied to reveal a different sequence. The process is repeated until all 40 starting sequences are revealed.

The transfer of DNA fragments to nylon or other suitable support materials, such as nitrocellulose, is an essential component of all DNA hybridization techniques including in addition to multiplex sequencing, chemiluminescence detection, DNA finger printing, and various other techniques that are not necessarily DNA sequencing procedures. The DNA fragments are transferred to deposition membranes either by various elution techniques or by electrophoresing the bands completely off the gel onto a moving deposition membrane, a process called direct blotting.

Conventional direct blotting devices utilize a deposition membrane attached to a conveyor belt in the lower buffer chamber that remains totally submerged during electrophoresis. Such devices do not allow detection or downstream processing except by physical removal of the nylon or other membrane from the conveyor belt. The almost total submersion of the deposition membrane makes detection and processing in the electrophoretic device proper a difficult if not impossible task that must take place through the liquid buffer.

A component of the instant invention is a unique drum electrophoresis unit which allows direct blotting of the sequence ladders onto a nylon or other suitable deposit membrane affixed to a rotating drum. The deposition interface between the end of the plate supporting the gel and the membrane covered drum is not submerged in buffer but is removed to a distance away from the lower buffer chamber. This invention conveys significant advantages to the system as compared with submersed interface and conveyor belt direct blotting systems.

In the instant invention the drum is only partially immersed in the bottom buffer chamber and can easily be removed without disturbing the deposition membrane. The drum can then be moved intact to suitable downstream detection and processing units which can be rugged and reliable because of the enabling geometry of the deposition membrane attached to the drum.

The deposited DNA ladder in the instant invention, spends considerable time in the open non-buffer space outside of the lower buffer chamber. Because of lack of buffer in this space processing devices such as UV fixing lamps or radiation or florescence detection devices can be built into the electrophoresis device that allow detection and part or all of the downstream processing to occur in a single device without moving the drum. Alternatively, the drum can be easily removed with attached membrane and easily moved to specially designed downstream detection and processing units.

Productivity is currently limited by the amount of material that can be processed at one time—that is, during a single run. The lower limit for width of a single slab-gel loading well on a conventional DNA sequencing apparatus is approximately 4 mm, with a required spacing between adjacent wells of about 0.2 mm. If these dimensions are decreased to increase data compaction, significant ladder drift and data cross talk occur during electrophoresis which severely limits the accuracy of the data. With these limitations only about 48 lanes can be run on a single nylon membrane with about 200 mm of effective deposition surface affixed to the drum of the instant invention.

Another aspect of the instant invention is a component called a ribbon channel plate which provides increased productivity in terms of data density packed into a single run with concomitant increases in sequencing speed and data resolution. The ribbon channel plate consists of a plate with a series of adjacent micro channels which can replace the conventional slab gel. When cast with gel, each microchannel represents an electrophoresis lane isolated and independent of its neighbors which eliminates the common problem of drift and interference that limits data compaction of standard continuous slab gels when loading density is increased.

Other aspects of the device enables efficient processing in the identification of DNA sequences by any one of the available detection methods including multiplex sequencing. Still another aspect is an increase of speed in DNA sequencing because of the ability to run at higher electric fields with efficient temperature control of the ribbon channel plate.

The human genome consists of three billion bases distributed over 24 chromosomes. The invention herein described, under optimal conditions can process about 24,000 (48 reaction sets (with each reaction set occupying 4 lanes), X 500 bases per sequence length) bases per run. The adaptation to multiplexing increases the output by about another factor of 40 per run to 96,000 data points. This estimation is based upon the number of distinct multiplexing (40) vectors reported by Church. The throughput estimation is nearly the million or so bases per run needed for efficient completion of the Human Genome Project in a reasonable time frame.

Other technologies which promise more resolution and speed such as ultra-thin gels and the use of longer glass plates with wedged spacers are physically limited in data compaction by geometry. Gel-filled capillaries presently offer an increase in resolution and dramatically decreases in running time but are also limited because of the technical complexities of creating large arrays and the difficulty in manufacturing and the limited lifetime of capillaries which can not be easily recast. Both these technologies employ on-the fly florescence detection through appropriate windows near the end of the electrophoresis gel. On-the-fly detection demands labeling of the ladder during the sequencing chemistry and are for all practical purposes incompatible with multiplexing where labeling occurs after electrophoresis utilizing specific labeled hybridization probes.

Multiplexing technology, at the present stage of development, is tedious and requires processing of individual nylon or nitrocellulose membranes upon which the multiplexed ladders are affixed. After standard slab gel sequencing the spatially resolved ladders need to be blotted out of the gel onto deposition membranes prior to the multiplexing development procedures involving labeled sequence specific DNA probes. Direct blotting runs the ladders completely off the electrophoresis gel onto a moving substrate of deposition membrane, and has the advantage of additional resolution since all the fragments must run the total length of the gel which affords more separation before being eluted onto the membrane. The downstream processing problems associated with handling and repeated washing and probings necessary for multiplexing are not, however, alleviated by direct blotting alone but are greatly reduced by using the drum device of the instant invention.

BRIEF DESCRIPTION OF THE DRAWINGS

FIG. 5a: Is a top view of the pressure plate.

FIG. 5b: Is a side view of the pressure plate.

FIG. 7a: Is a top view of the ribbon channel plate.

FIG. 7b: Is a side view of the ribbon channel plate.

FIG. 8a: Is a top view of the cover plate.

FIG. 8b: Is a side view of the cover plate.

DESCRIPTION OF THE PREFERRED EMBODIMENTS

The instant invention is an electrophoresis system that combines the advantages of micro separation previously obtained with gel-filled capillaries and ultra-thin gels coupled with a new approach to direct blotting.

Figure 1:
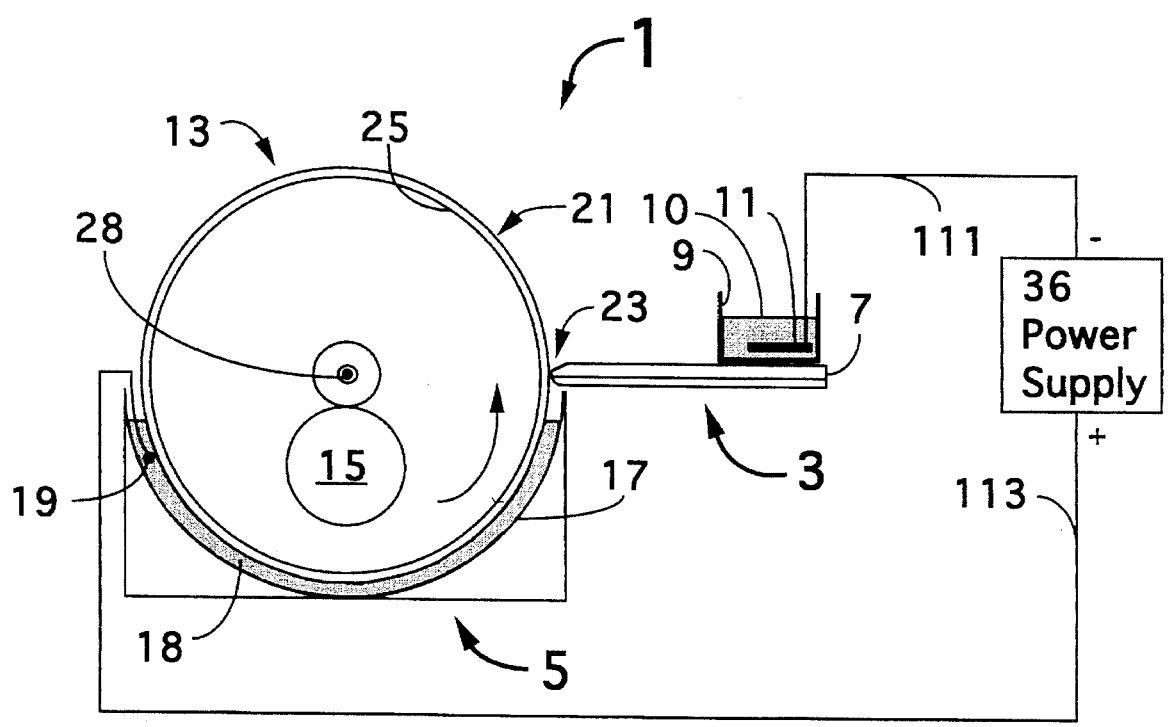
FIG. 1: Is a schematic representation of the basic components for the preferred embodiment of the instant invention.

FIG. 1 illustrates the instant invention, which is a ribbon channel rotating drum electrophoresis device 1. This device consists of two main components, the gel support unit 3 and the drum assembly 5. The gel support unit 3 is illustrated in FIG. 1 in the horizontal position. Horizontal refers to the placement of the gel support unit 3 relative to the rotational axis of the drum 13, which is also in the horizontal plane. This configuration places minimum distance between the lower buffer chamber 17 and the plate-drum interface 23 thus minimizing drying and other interface associated anomalies. A vertical position of the gel support unit 3 is also possible, and is discussed in more detail supra.

The gel support unit 3 includes the plate assembly 7, the upper buffer chamber 9, and the upper electrode 11. The upper buffer chamber 9 contains a first buffer solution 10, and has a bottom portion 8.

The drum assembly 5 is comprised of a rotating drum 13 a stepper motor drive assembly 15, the lower buffer chamber 17, a lower electrode 19. The drum assembly 5 is typically mounted on a base plate 6. The drum 13 which rigidly supports the deposition membrane 21 is rotated by the stepper motor drive assembly 15 while being partially submerged in the lower buffer chamber 17.

Figure 2:
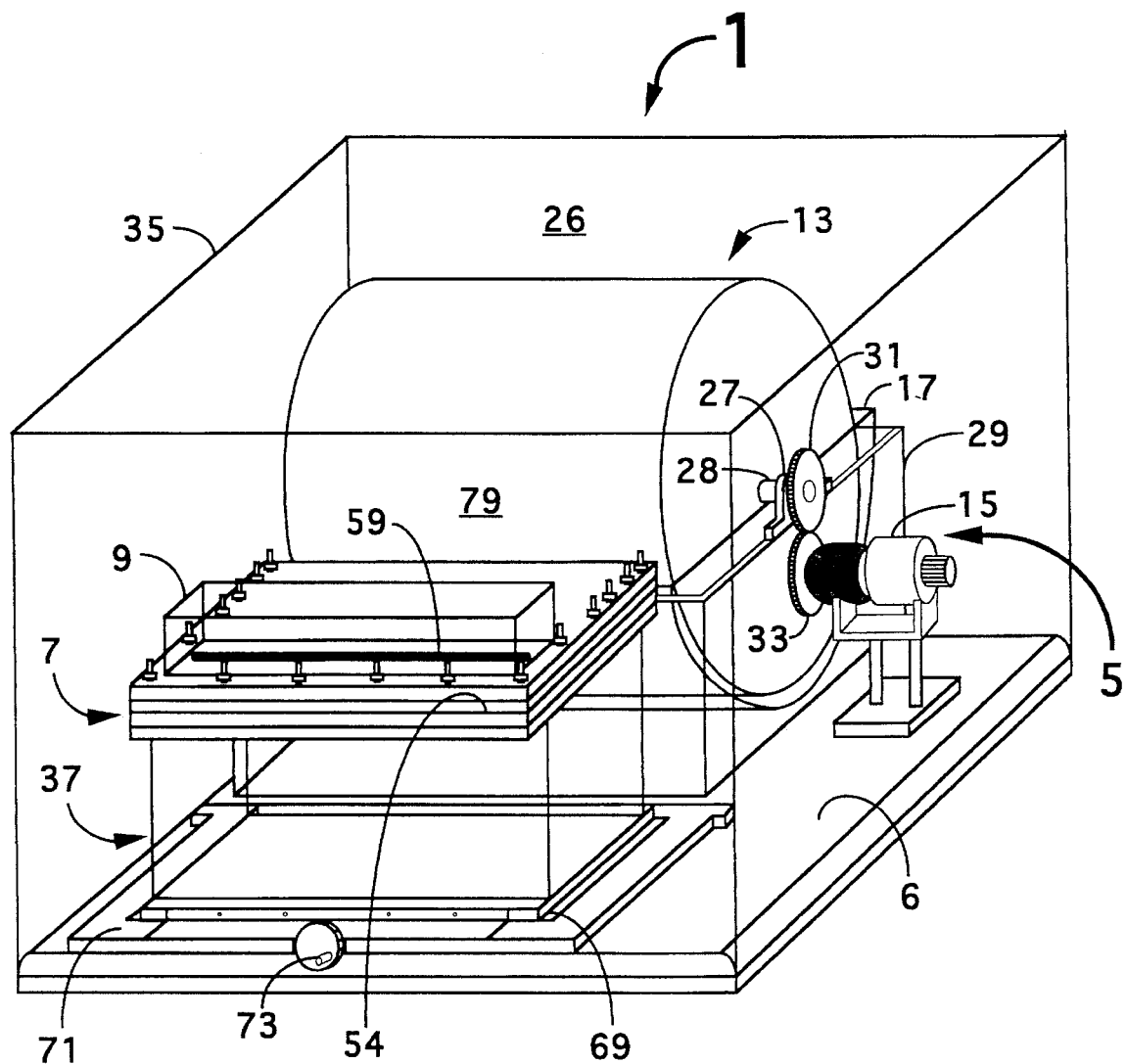
FIG. 2: Is an isometric representation of the preferred horizontal embodiment of the gel support unit of the electrophoresis apparatus.

FIG. 2 is an isometric illustration of the preferred horizontal embodiment of the ribbon channel plate rotating drum electrophoresis device 1.

Plate-Drum Interface

Electrical continuity is established between the lower electrode 19 and upper electrode 11 at the plate-drum interface 23 where the plate assembly 7 and the deposition membrane 21 on the drum surface 25, are in close physical proximity of each other, and an electrical junction through a thin layer of conducting buffer. This region is called the plate-drum interface 23. The interface between the deposition membrane 21 and the plate assembly 7 is thus removed from submersion in the lower buffer chamber 17.

Rotation of the Drum

The drum 13 is rotated at a controlled rate during electrophoresis by the stepper motor drive assembly 15 away from the lower buffer chamber 17 such that the DNA fragments are deposited on the deposit membrane 21 attached to the drum surface 25.

Referring again to FIG. 2 the drum 13 rotates on an drum axle 28 that is supported on each end by bearings. Sealed bearings have proved to be the most practical in the constructed embodiments. The bearing housings 27 are fastened by quick release connections (not shown) to the drum support unit 29 for the easy removal of the drum 13. The engaging gear 31 attached to the drum axle 28 of the drum 13 easily meshes with the drive gear 33 attached to the stepper motor drive assembly 15. Such an arrangement is the most practical means achieved thus far for the accomplishments of all envisioned embodiments and will be a part of most all downstream processing and development devices where drum 13 rotation is desirable that is discussed supra. Embodiments utilizing timing belts and pulleys as a drum rotation means are also possible.

Vertical Embodiment Possible

Figure 3:
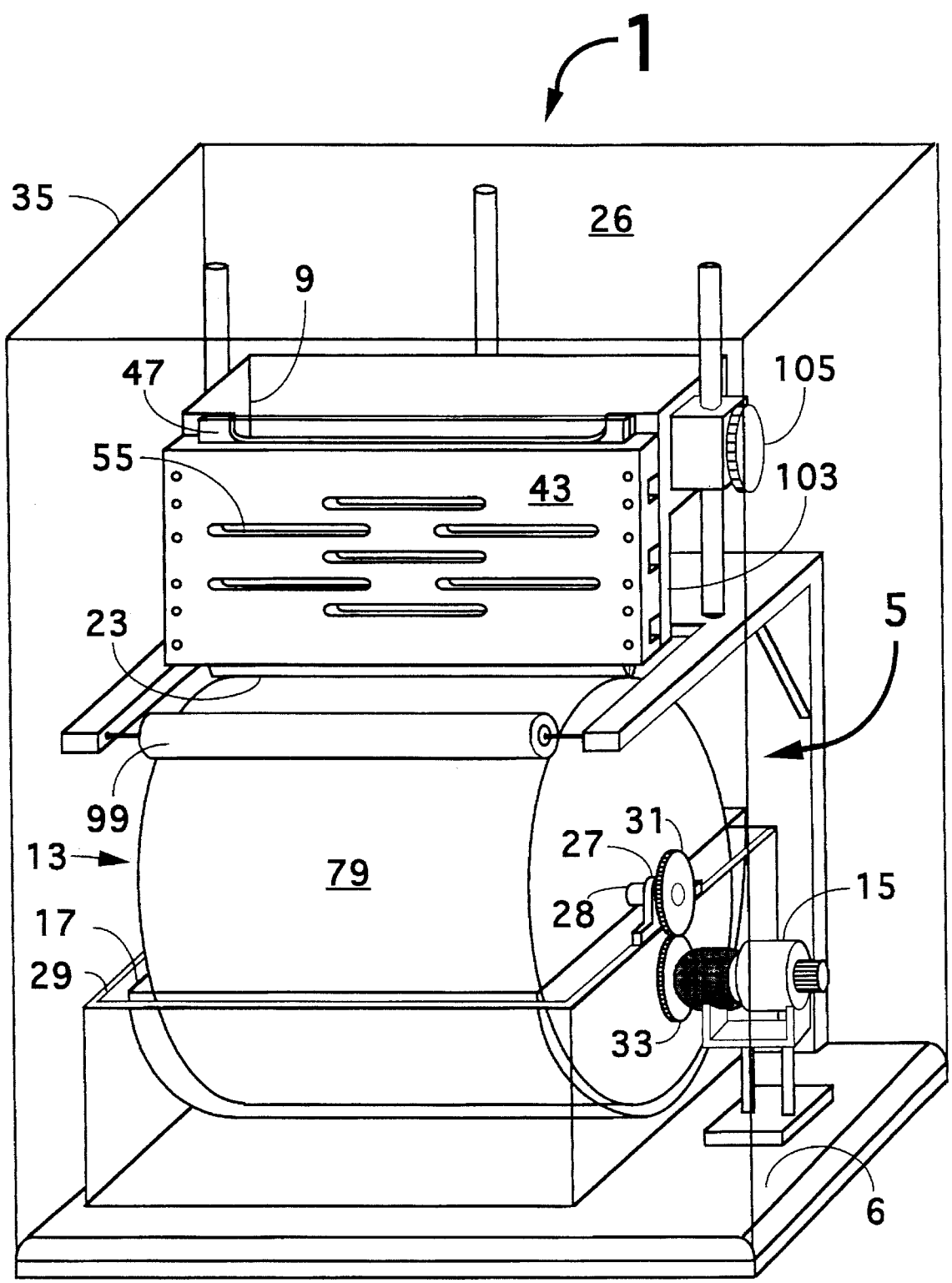
FIG. 3: Is an isometric representation of the vertical embodiment of the gel support unit of the electrophoresis apparatus.

The drum assembly 5 for both the preferred horizontal embodiment illustrated in FIG. 2 and the vertical embodiment illustrated in FIG. 3 are very similar except for those parts specifically related to accommodating the gel support unit 3. A hinged or form fitting cover 35 is an optional part of the devices described herein. The cover 35 provides an electrical interlock between the power supply 36 and the electrophoresis device 1 for safety. The cover 35 can also be a place where equipment specific to downstream detection and processing can be housed in the non-buffer space 26.

Plate Assembly and Support Table

Figure 4:
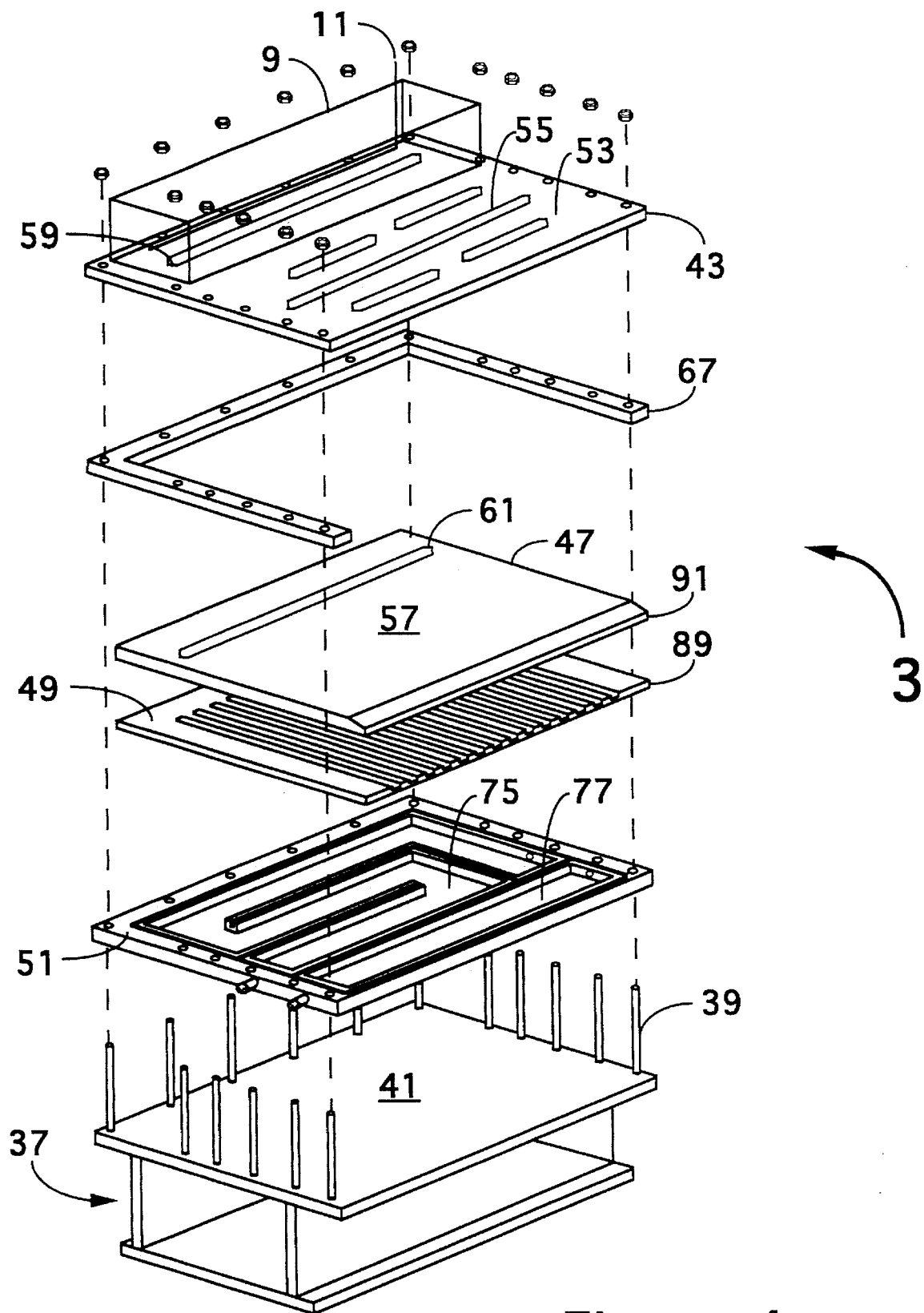
FIG. 4: Is an isometric representation of an expanded view of the components of the gel support unit.

FIG. 4 is a illustration of an expanded parts breakdown of the plate assembly 7 and support table 37. The system is held together by threaded nylon studs 39 evenly dispersed and countersunk into the upper platform 41 of the support table 37. The pressure plate 43 is secured by nylon hex head nuts 45 to the threaded nylon studs 39 of the support table 37. Sandwiched between the pressure plate 43 and the support table 37 are the cover plate 47, the ribbon channel plate 49, and the temperature control plate 51. The pressure plate 43 is continuous with the upper buffer chamber 9 which contains the upper electrode 11. The upper buffer chamber 9 is typically mounted to the top of the pressure plate 43 along its bottom portion 8, which is typically a portion of the upper surface 53 of the pressure plate 43.

The support table 37 typically has a receiving aperture 54 into which the plate assembly 7 is inserted.

The upper surface 53 of the pressure plate 43 has a multiplicity of horizontal slits 55 which allow access to the upper surface 57 of the cover plate 47 for temperature monitoring during a sequencing run. The lower surface 58 of the cover plate 47 fits against the upper surface of the ribbon channel plate 49. The access slot 59 in the upper buffer chamber 9 gives access to the ribbon channel plate 49 through an identical access slot 61 in the cover plate 47. The access slot 59 can also be in the bottom portion 8 of the upper buffer chamber 9. This arrangement is what allows the upper buffer chamber 9 and the plate assembly 7 to be communicably attached. The bottom surface of the pressure plate 63 illustrated in FIG. 5a has recessed channels with a neoprene O-ring gasket 65 that leak seals the upper buffer chamber 9 around the access slot 61 in the cover plate 47.

Referring again to FIG. 4, the U-shaped spacer bar 67 serves to align the ribbon channel plate 49 to the cover plate 47 which together with the plate assembly 7 comprise the gel support unit 3.

Figure 6B:
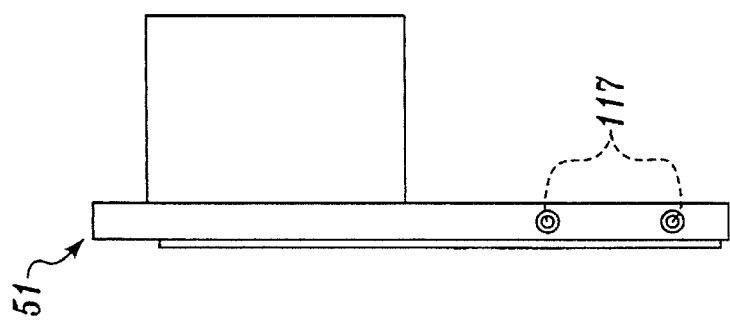
FIG. 6b: Is a side view of the temperature control plate.
Figure 6A:
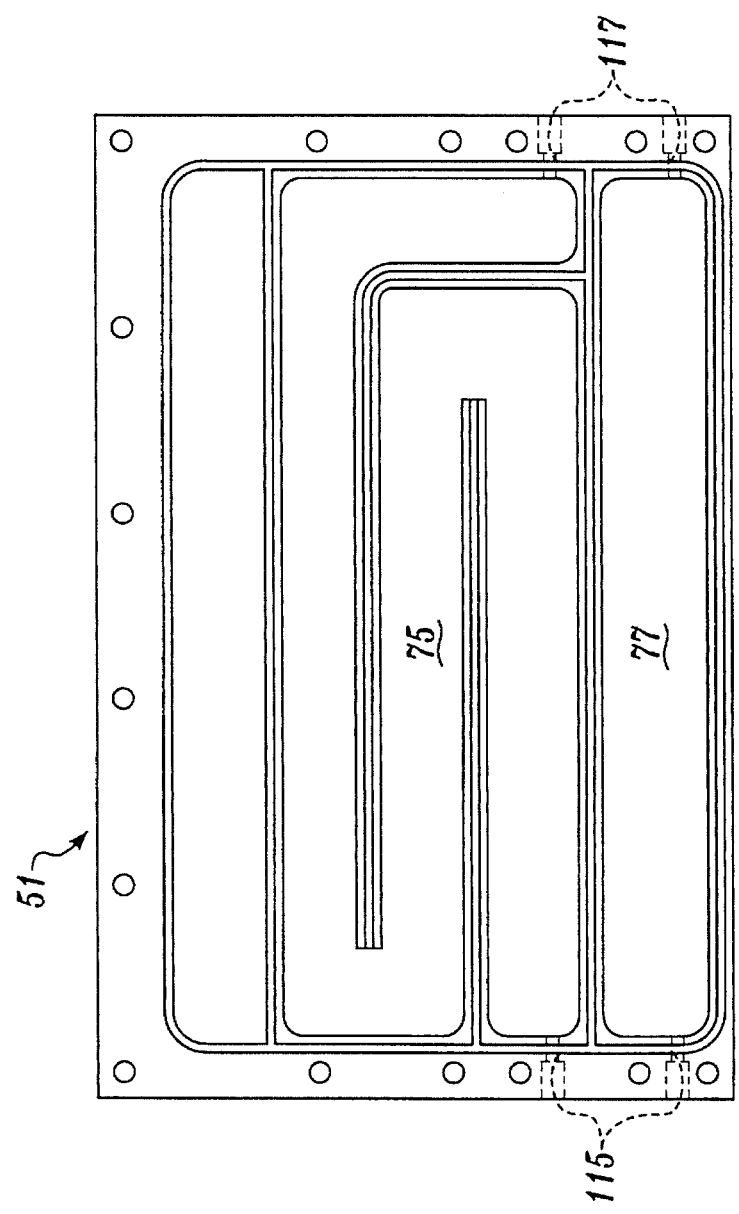
FIG. 6a: Is a top view of the temperature control plate.

FIG. 6a and 6b shows in detail the temperature control plate 51 having a first chamber 75 and the second chamber 77 through which liquids at different temperatures can be circulated. The first chamber 75 controls the temperature over the majority length of the ribbon channel plate 49. While the second chamber 77 maintains the region near the plate-drum interface 23 at the same temperature as the deposition membrane surface 79 to avoid interface anomalies due to large temperature differentials across the plate-drum interface 23. The baffles and walls of chambers 75 and 77 have recessed neoprene gaskets 81 which form a liquid tight seal with the bottom surface (not shown) of the ribbon channel plate 49 once the plate assembly 7 is put together.

The ribbon channel plate 49 and the cover plate 47 are illustrated in detail in FIGS. 7a and 8a respectively. The ribbon channel plate 49 in FIG. 7a is not to drawn scale for the sake of clarity, showing much fewer than the present 192 individual ribbon channels 83. The ribbon channels 83 can be etched, machined or cast in glass, ceramic or other material compatible with polyacrylamide or other suitable gel 84. The preferred material for the ribbon channel plate 49 is the ceramic Mycor™ manufactured by Corning Glassware which is machinable to close tolerances and is extremely compatible with polyacrylamide gel. The upper surface of the ribbon channel plate 85 illustrated in FIG. 7a and the underside (not shown) of the cover plate 47 in FIG. 8a need to be faced or polished to a true flatness. When fitted together they should not allow liquid to flow between the channel walls 87 illustrated in FIG. 7a that separate the individual ribbon channels 83 after the gel has polymerized in the plate assembly 7. A thin treated polyester gasket (not shown) can be used if needed between the ribbon channel plate 49 and the cover plate 47 illustrated in FIGS. 7a and 8a respectively. The preferred material of the cover plate 47 is Pyrex™ glass. FIG. 7b and FIG. 8b are side views of the ribbon channel plate 49 and the cover plate 47 respectively, showing the beveled edges 89 and 91 respectively, that makeup the plate portion of the plate-drum interface 23 illustrated in FIG. 1. Both the cover plate 47, illustrated in FIG. 8a and the ribbon channel plate 49 illustrated in FIG. 7a should be worked together as a unit when polishing and making the bottom edges flat, to assure complete trueness.

Figure 9A:
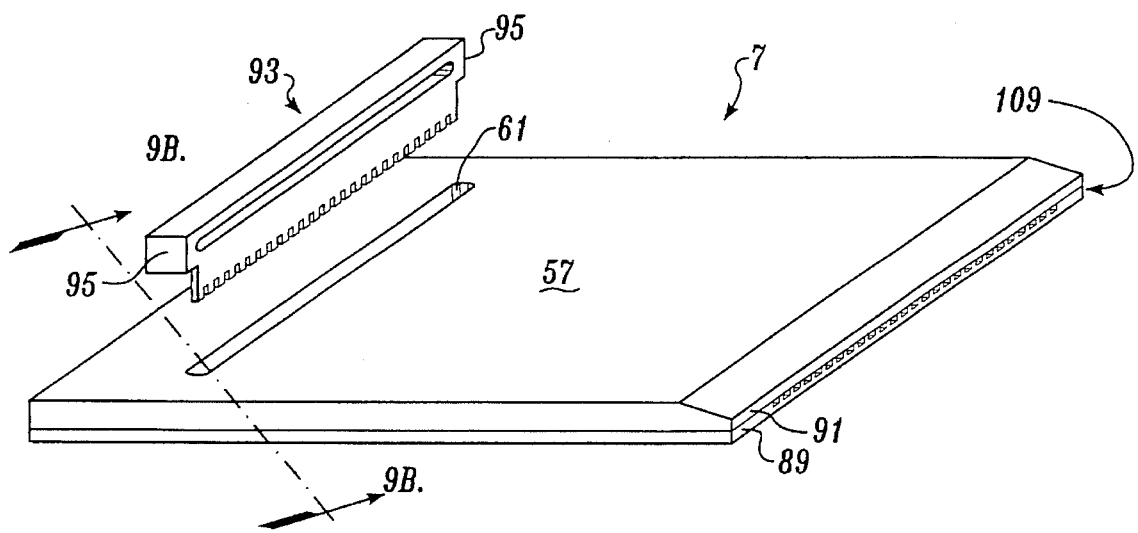
FIG. 9a: Is a isometric view of the plate assembly with the gel displacement comb positioned for insertion.
Figure 9B:
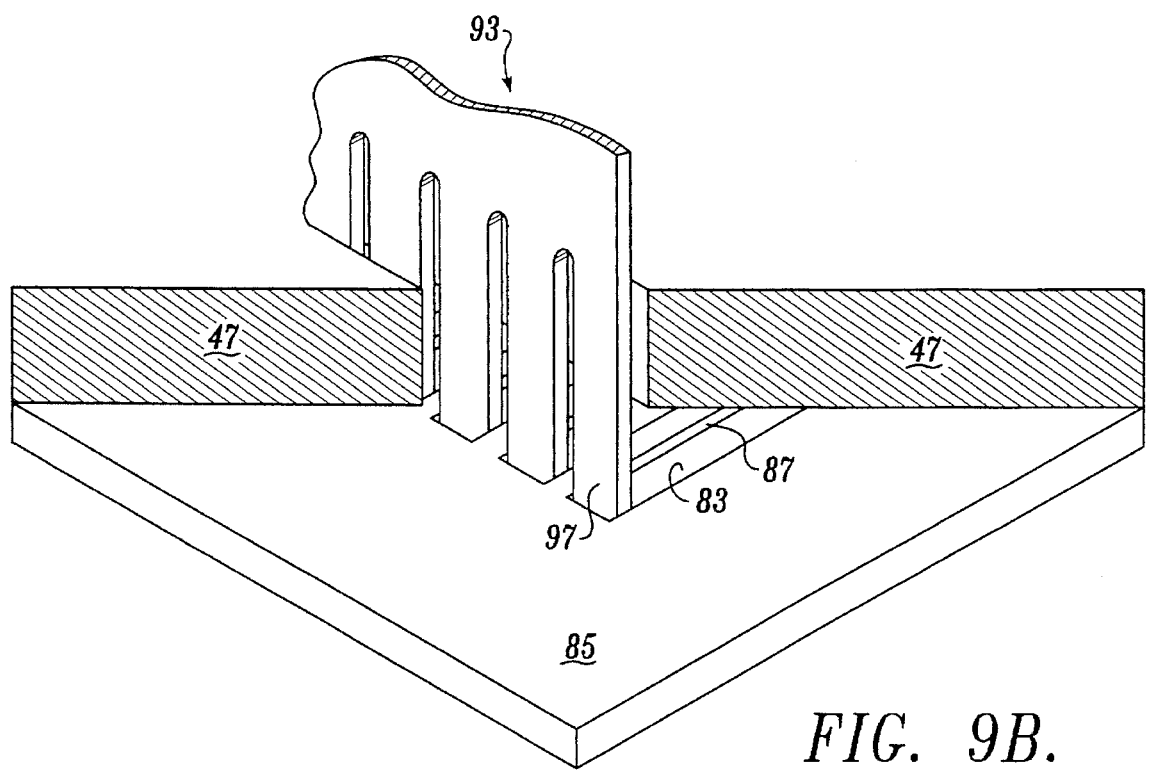
FIG. 9b: Is a cross-sectional view of the plate assembly along line 9b—9b illustrating the gel displacement comb in the inserted position.

FIG. 9a illustrates in detail the orientation of the gel displacement comb 93 and its relationship to the plate assembly 7. The gel displacement comb 93 has tabs 95 on each end that slide into recesses (not shown in detail) within the upper buffer chamber 9 illustrated in FIG. 4. Referring to again FIG. 9a The individual comb teeth 97 fit snugly into each ribbon channel 83 blocking gel from a small upper portion of the channel, thus reserving a space for sample loading. FIG. 9b shows a close up cross section view of the comb teeth 97 inserted into the ribbon channels 83. Again the dimensions in FIG. 9a and FIG. 9b are exaggerated for clarity.

Figure 9C:
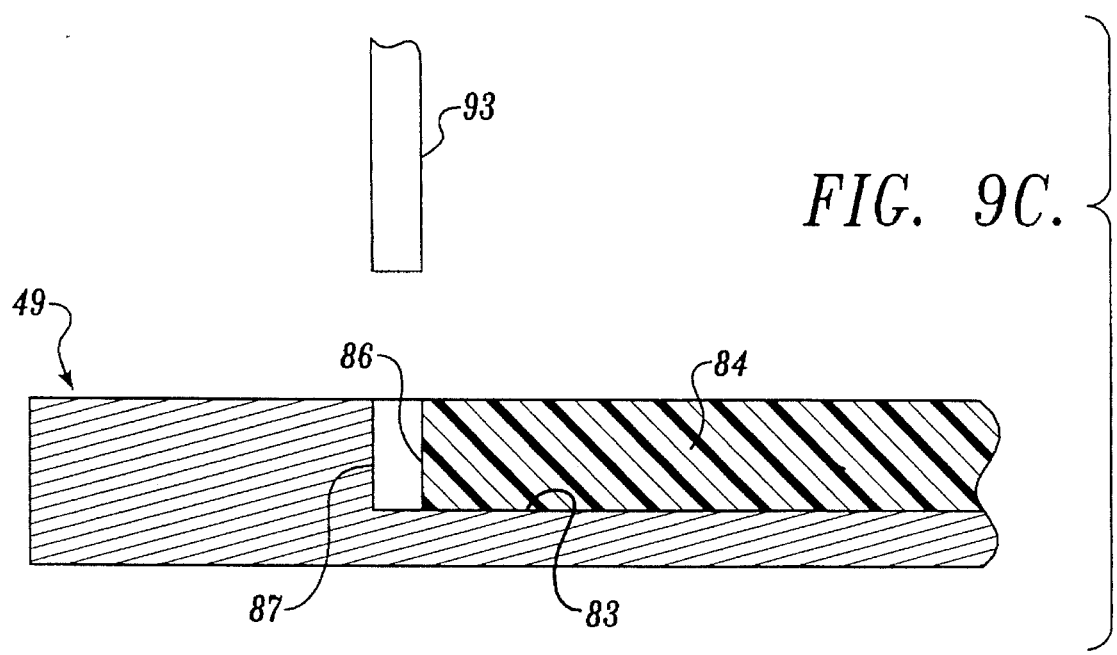
FIG. 9c: A cross-sectional view of the ribbon channel plate illustrating a receiving well.

Once the gel has polymerized in the ribbon channels 83 the gel displacement comb 93 is removed leaving sample receiving wells 86 as illustrated in FIG. 9c. The specific type of sample loading device is not critical to the practice of the instant invention, however, this is typically accomplished with individual or ganged fine gauge glass barrel syringes.

Utilization of the Vertical Embodiment

FIG. 3 illustrates an overall view of the vertical embodiment of the instant invention. The vertical placement of the gel support unit 3, the ribbon channel plate 49 and the cover plate 47 of the gel support unit 3 are of different construction than similar components in the preferred horizontal embodiment illustrated in FIG. 2. Referring again to FIG. 3 There are no access slots through the buffer chamber or the cover plate 47, since the sample must be loaded vertically from the top. This substantially limits the dimensionality of the channels of the ribbon channel plate 49 whose depth are strongly determined by the dimensionality of the loading device and gel displacement comb 93 which must fit physically within the ribbon channels 83, entering from a vertical aspect rather than the horizontal aspect of the preferred embodiment.

At times especially during long runs with the vertical embodiment the deposition membrane surface 79 has a tendency to dry and require support buffer from a wicker device 99 which delivers buffer at a controlled rate to the deposition membrane surface 79. Depending on what types of detection methods being used, application devices like the one described above may be employed for processing and developmental procedures taking place on the deposition membrane surface 79. The vertical arraignment of the plate assembly 7 creates an unfavorably large distance between the plate-drum interface 23 and the lower buffer chamber 17. Local drying of the deposition membrane surface 79, obligates the use of a buffer support underlayment 101 illustrated in FIG. 10 on the drum 13 and a wicker device 99 illustrated in FIG. 3 to assure wetting and proper electrical continuity during the run.

For average duration runs of about one to two hours, a wicker device 99 and/or buffer support underlayment 101 is oftentimes unnecessary in the preferred horizontal embodiment illustrated in FIG. 2. Referring again to FIG. 3, an elongated U shaped section is removed from the upper portion of the ribbon channel plate 49 providing buffer access and electrical continuity to the top aspect of the plate assembly 7 from the upper buffer chamber 9. The back of the plate assembly 7 mates to the vertical support structure 103 and the upper buffer chamber 9 with recessed neoprene gaskets (not shown). At the plate-drum interface 23, the distance between the plate assembly 7 and the deposition membrane surface 79 is controlled by vertical rack and pinion gear assemblies 105 located on each side of the upper buffer chamber 9.

Figure 10:
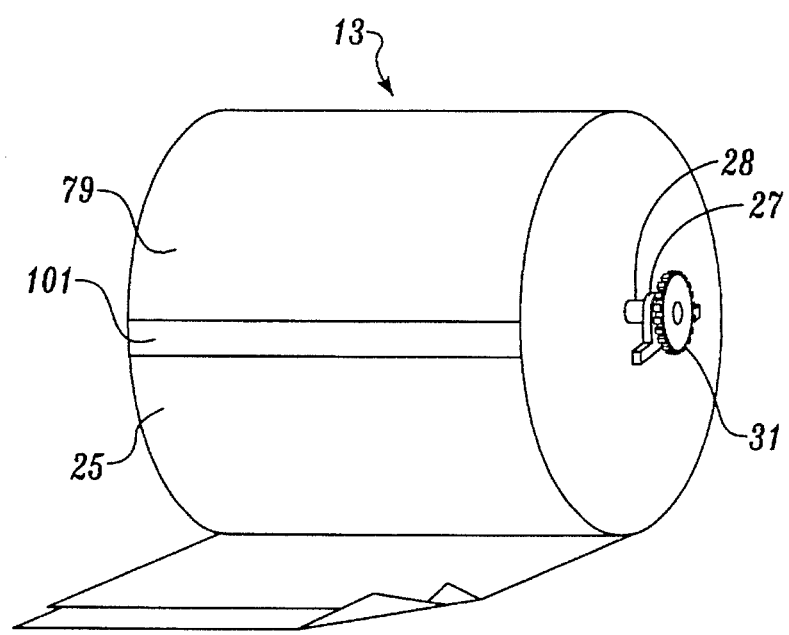
FIG. 10: Is an isometric view of the drum.

Now referring to FIG. 10, the drum 13 shape is unique and allows for easy handling of the attached deposition membrane 21. For example, a deposition membrane 21 onto which information is ultimately deposited discussed supra is flimsy when wet and direct handling of the can cause distortion of the information stored thereon. The drum surface 25 has been knurled to promote the wetting properties of the normally hydrophobic acrylic surface. Also illustrated the optional buffer support underlayment 101 that makes up the layer underneath the deposition membrane 21.

Figure 12:
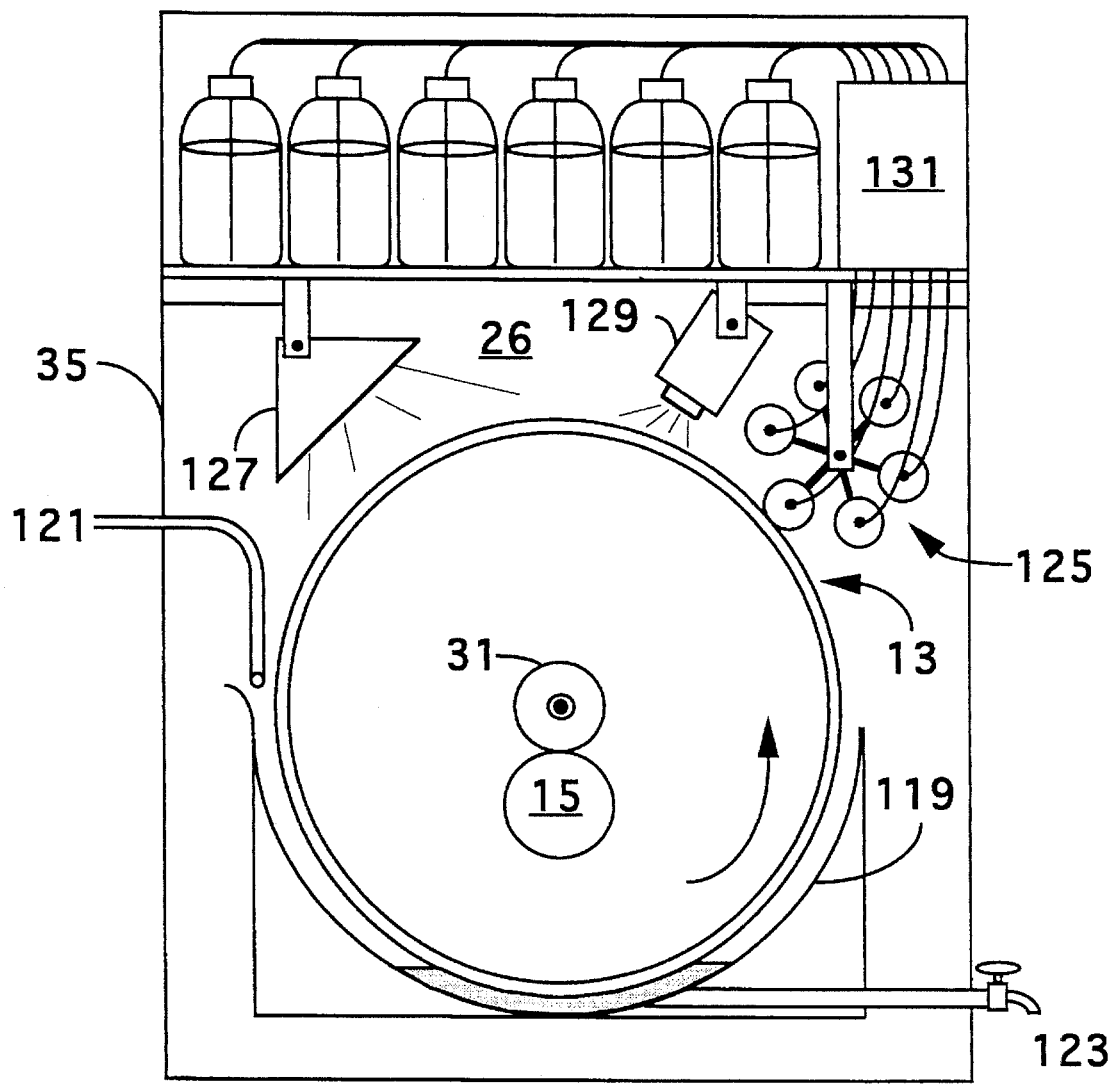
FIG. 12: Is a schematic representation of downstream processing devices.

The drum 13 has built in bearing housings 27 which slip fit onto the drum support unit 29 illustrated in FIG. 12. Bearings, and bearing mounts are also typically used but are not shown. The engaging gear 31 mounted to the drum axle 28 protrudes to the outside of the drum 13 allowing easy engagement with the drive gear 33 of the stepper motor drive assembly 15. This configuration allows easy insertion and removal of the drum 13 from the drum support unit 29.

The means of turning the drum 13 is not critical to the invention. The speed of rotation of the stepper motor drive assembly 15 and thus the rotational speed of the drum 13 is controlled by a microcomputer (not shown). Rotation speeds for the drum 13 are set during the run by measuring the velocity of electrophoresis of standard bromphenol blue and xylene dye bands.

The lower buffer chamber 17 is half cylindrical with a small annular space that is filled with a minimum volume of buffer. The receiving platform 71 has a built in runner bracket 107 and positioning guides 69 for the accommodating the base of the support table 37. The lateral movement of the plate assembly 7 is controlled by the rotary positioning screw 73.

Pouring the gel

The plate assembly 7 and support table 37 are assembled into a unit as illustrated in FIG. 4. Liquid gel 84 is poured into the plate assembly 7 through the access slot 61 in the cover plate 47 from the access slot 59 in the bottom of the upper buffer chamber 9. The protruding interface edge 109 of the plate assembly 7 is made up of the two beveled surfaces 89 and 91, and is wrapped in a loosely fitting Parafilm bag which catches excess liquid gel. Once the gel has polymerized the excess protruding gel will be cut flush with the interface edge 109 using a sharp razor blade. It is imperative that the cover plate 47 and the ribbon channel plate 49 be in perfect alignment at the interface edge 109. This is easily accomplished by aligning the cover plate 47 and the ribbon channel plate 49 with a straight edge (not shown) before the nylon hex head nuts 45 of the plate assembly 7 unit are completely tightened. The U-shaped spacer bar 67 will also help to align the ribbon channel plate 49 perfectly to the cover plate 47.

The gel displacement comb 93 illustrated in FIG. 9a is snapped into place with in the upper buffer chamber 9 illustrated in FIG. 4 before the gel polymerizes and carefully removed after the gel sets.

Figure 11:
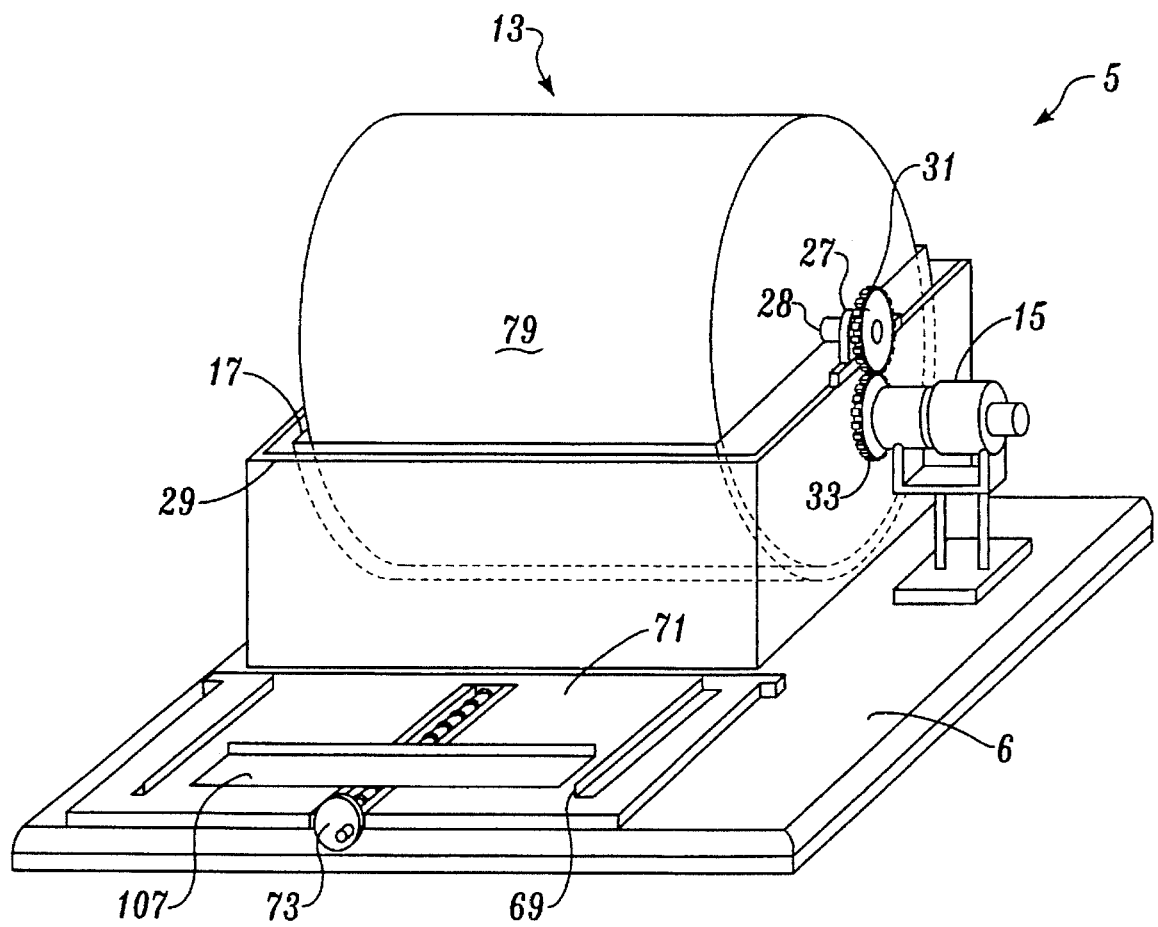
FIG. 11: Is an isometric view of the drum assembly.

In the preferred horizontal embodiments illustrated in FIG. 11, the plate assembly 7 attached to the support table 37 slides easily within special position guides 69 affixed to the receiving platform 71 of the drum assembly 5.

Wrapping the Drum

The drum 13 illustrated schematically in FIG. 10 is wrapped with buffer supporting underlayment 101 (optional) followed by the buffer soaked deposition membrane 21. The buffer supporting underlayment 101 is typically chromatography filter or blotting paper. The drum assembly 5 unit illustrated in FIG. 11 without the plate assembly 7 and support table 37 is used during this process. Buffer is placed in the lower buffer chamber 17 and the absorbent buffer support underlayment 101 and the deposition membrane 21 are affixed at the joining seam with waterproof sequencing tape to the drum 13. The two substrates are individually rolled onto the drum surface 25 with the use of a common kitchen rolling pin affixed by the handles to each end of the drum axis with large rubber bands (not shown). Once the buffer supporting underlayment 101 and the deposition membrane 21 are positioned into place and free from wrinkles they are then affixed to the drum 13 with waterproof sequencing tape. The prepared drum 13 is further equilibrated with the lower buffer solution 18 by low speed rotation with the stepper motor drive assembly 15 for 10–15 minutes.

Electrophoresis Circuit

Referring to FIG. 1, the electrical circuit required for electrophoresis is obtained from the power supply 36 through a first voltage lead 111 to the upper electrode 11, through the first buffer solution 10 in the upper buffer chamber 9, through the micro gel ribbons cast in the individual ribbon channels 83 to the plate-drum interface 23, through the deposition membrane 21 and the buffer support underlayment 101, around the drum surface 25, through the second buffer solution 18 in the lower buffer chamber 17, through the lower electrode 19 and finally to a second voltage lead 113, that is in turn connected to the power supply 36 as illustrated schematically in FIG. 1.

Deposition Membrane—Plate Assembly Interface

The plate-drum interface 23 between the interface edge 109 of the plate assembly 7 and the deposition membrane surface 79 is an important aspect for the successful practice of the instant invention. Best results will be achieved when a small buffer cushion is present at the point of contact where the interface edge 109 of the plate assembly 7 comes in close proximity of the deposition membrane surface 79. The narrow distance between the deposition membrane surface 79 and the interface edge 109 of the plate assembly 7 supports a thin horizontal column of liquid so that a liquid buffer meniscus (not shown) is present in the plate-drum interface 23. Tolerances between the interface edge 109 of the plate assembly 7 and the deposition membrane surface 79 should be in the order of 0.2 mm or less. Here, too small a clearance at the plate-drum interface 23 may cause tearing of the deposition membrane 21 by catching it with the interface edge 109 during rotation of the drum 13. Too large a clearance will cause loss of electrical conductivity and the forming of air bubbles that interfere with proper operation.

It is not necessary for the interface edge 109 to make physical contact with the deposition membrane surface 79 as long as the liquid buffer meniscus is present. This liquid buffer meniscus allows the system to accommodate small imperfections in the drum surface 25 and the deposition membrane surface 79 as well as providing an escape path for transient gas bubbles. However, as the clearance of the plate-drum interface 23 gap increases so does interface instabilities. Interface instabilities include sensitivity to temperature gradients, evaporative drying, and sensitivity to apparatus vibrations. Similar problems can be caused by improper alignment of the interface edge 109 to the deposition membrane surface 79.

As is apparent from FIG. 2, rotation of the rotary positioning screw 73 causes linear motion of the interface edge 109 (not shown) with respect to the deposition membrane surface 79. Using this mechanism the plate edge is brought to touch the deposition membrane surface 79 and backed off until light from a small flashlight is first visible through the plate-drum interface 23. In this position the drum 13 should then be slowly rotated through the expected extent of the electrophoresis and checked for snagging of the deposition membrane surface 79. The drum 13 can usually be backed off a little more to relieve snagging of the deposition membrane surface 79 if encountered without losing the liquid buffer meniscus.

Electrical Conduction Aid for Drum

Referring now to FIG. 10, electrical continuity can be aided by a buffer supporting underlayment 101, which is typically a layer of filter paper or other absorbent material that is placed between the drum surface 25 and the deposition membrane 21.

Use of buffer supporting underlayment 101 is optional and dependent upon the degree of hydrophilicity of the knurled drum surface 25, the absorbency and retention capabilities of the deposition membrane 21, and the distance of the plate-drum interface 23 from the liquid buffer level in the lower buffer chamber 17. The shorter the distance from the surface of the solution in the lower buffer chamber 17 to the plate-drum interface 23, the less local drying of the deposition membrane surface 79. Suitable buffer supporting underlayments 101 include chromatography paper, blotter paper, or sponge sheets. Suitable deposition membranes 21 include charged and uncharged nylons, nitrocellulose, polyvinyl-fluoride, and similar membranes suitable for the deposition of nucleic acids.

Use of Wicker Devices To Prevent Drum Drying

The large surface area of the drum 13 and the open traveling distance before sequence deposition at the plate-drum interface 23 sometimes leads to local drying of the deposition membrane surface 79. This is especially true during long runs with slow drum-rotation speeds when using the vertical configuration illustrated in FIG. 4. The wicker device 99 illustrated delivers a controlled continual flow of buffer or other solutions to the deposition membrane surface 79 through a sponge-filled perforated roller. Only one wicker device 99 is necessary to aid with maintaining drum 13 and deposition membrane 21 wetness during electrophoresis when using the vertical configuration. Several wicker devices of this general design can be conFIG. d together to control the flow of reagents and washing solutions for use in automated downstream multiplexing and chemical detection processing procedures.

The drum drying problem is greatly alleviated in the preferred horizontal configuration illustrated in FIG. 3 where the distance from the surface of the second buffer solution 18 to the plate-drum interface 23 is minimized and in most cases the wicker device is not necessary. It should be noted that the drum 13 is rotated in the direction toward the plate-drum interface 23 and away from the lower buffer chamber 17.

Construction of the Unit Components

Referring again to FIG. 9a of the gel support unit that consists of the ribbon channel plate 49, and the cover plate 47. The ribbon channel plate 49 illustrated in FIG. 7a can be machined with various channel depths and widths with great control over the gel ribbon dimensions. Typically the depth <0.2 mm is less than the width <0.4 mm to preserve some band like quality to the resolved fragments and thus the name "ribbon channel". These channel dimensions are limited only by fabrication limits and loading considerations of the small sample size, and not by intrinsic factors such as data degeneration due to lane drift and cross talk that limit thin slab gels. As illustrated in FIG. 9a, the interface edge 109 of the plate assembly 7 has been beveled by machine-grinding, and polishing. The minimal bottom is ground to a true flatness by working both plates together as a unit.

If the plate assembly 7 is to be used without a gasket the under surface of the glass cover plate 47 should also be ground to a true flatness. The inside surface of the access slot 61 should be polished to insure easy insertion and removal of the gel displacement comb 93 and sample loading devices (not shown). The polishing will also help prevent cracking of the cover plate 47 across the access slot 61 which can occur due to uneven pressure applied by the upper pressure plate 43 illustrated in FIG. 4 or by extreme temperature variations during the electrophoresis run if temperature control is inadvertently lost.

Use of Gasket Material

Referring to FIG. 4 the physical and electrical isolation of one channel from another can sometimes be aided by a thin transparent polyester gasket (not shown) placed between the ribbon channel plate 49 and the cover plate 47. The gasket is useful when using glass cover plates 47 with an uneven bottom surface and with ribbon channel plates 49 where slight irregularities along the upper surfaces of the channel walls 87 exist.

However, it should be noted that experiments have indicated the functioning of the ribbon channel plate 49 is not dependent on using a gasket. Actually, successful DNA sequencing and assemblage of the plate assembly 7 is much simpler when a gasket is not used. Transparent 0.1 mm thick polyester sheets are a suitable gasket to obtain seals between the ribbon channel plate 49 and the glass cover plate 47. Gaskets that are highly deformable are not desired here since under slight pressure, the excess gasket material will compete with gel in the ribbon channels 83. The polyester gaskets should be treated with a 6N KOH and then silated with Trimethoxysilylpropyl-methacrylate.

Temperature Control Plate

Referring now to FIG. 6a the temperature control plate 51, through which a temperature controlling liquid can be circulated is sealed to the back of the ribbon channel plate 49 using recessed neoprene gaskets 81. The temperature of the plate assembly 7 can be controlled by circulating a temperature controlled fluid through the two chambers 75 and 77 via inlet ports 115 and outlet ports 117. The forward section of the plate assembly 7 illustrated in FIG. 9a; i.e., that portion nearest the plate-drum interface 23, can be separately thermostated from the bulk of the gel support unit. This allows the bulk of the plate assembly 7 to be run at elevated temperatures of 40°–60° C., while maintaining the forward section of the gel support unit at a temperature close to the deposition membrane surface 79, typically about 18°–20° C. Reducing the temperature gradient between the plate assembly 7 and the surface 79 of the deposition membrane 21, will act to minimize convective mixing during deposition at the plate-drum deposition interface gap. It is apparent that there are alternatives to temperature control using electronic devices that can replace circulating fluid.

Use of Comb Assembly

The gel displacement comb 93 illustrated in FIG. 9a is a means for blocking off upper sections of the ribbon channels 83 from receiving gel and thus providing a sample loading space or well. Here it is important to realize that insertion of the gel displacement comb 93 when the plate assembly 7 illustrated in FIG. 4, is put together requires the gel displacement comb 93 to be inserted through the access slot 59 through the bottom of the upper buffer chamber 9. The gel displacement comb 93 is inserted through the access slot 61 in the cover plate 47 such that the individual comb teeth 97 protrude into the bottom of each ribbon channel 83 as illustrated in FIG. 9b. This is significantly different than using similar combs to form sample receiving wells 86 in slab gels. The gel displacement comb 93 is snug fitting within the ribbon channels 83 and the access slot 61 cut through the cover plate 47. The gel displacement comb 93 is treated with a siliconizer spray prior insertion to ensure easy withdrawal without pulling out clinging fragments of gel. The gel displacement comb 93 is rigidly snapped into position with in the lower buffer chamber 17 prior to the polymerization of the liquid gel. The tabs 95 on each end of the gel displacement comb 93 slide into recesses in each end of the upper buffer chamber 9 further stabilization.

The comparatively rugged isolation of each channel's loading well from its neighboring loading well and the "snap in fit" allows the design of an albeit miniature but rugged ganged loading manifold (not shown).

Downstream Processing

Collectively the events that occur after electrophoretic deposition are called downstream detection and processing.

Downstream Process Within Apparatus

In the upper portion of the instant invention a non-buffer space 26 exists that is suitable for processing and detection devices. Detection devices may include; reagent wickers, UV fixing and drying lamps and detection devices such as photoelectric and radiation counting devices. These devices can be attached to the to the electrical interlocking cover 35 or attached to supporting members within the non-buffer space 26 of the device.

Downstream processing in a Separate Device

Possible embodiments of the instant invention may include downstream events occurring in the same overall device as electrophoresis. Alternatively some or all of these events can occur in similar devices devoid of electrophoresis components specifically designed for downstream events as depicted conceptually in FIG. 12. Such devices may vary in design detail and function but all are designed to easily accommodate and manipulate the drum 13 and attached deposition membrane 21, transferred from the electrophoresis device 1.

The reagent interchange tray 119 has an inlet port 121 and a outlet port 123 for reagent exchange. Various buffer reagents can be cycled during various washing and rinsing steps. Here the reagent wicker device 125 has several positions where different hybridization probes and other high concentration low volume reagents can be applied to the deposition membrane surface 79. Various drying and fixing lamps 127 and detection devices 129 can be placed in the non-buffer space 26 located in the upper portion of the electrophoresis device 1. Reagent delivery and processing events can be facilitated by various standard pumps, reservoirs, timers and other liquid control and handling devices 131 known to those skilled in the art. The events during processing and detection are real-time computer controlled systems which are designed for the ease in automation of downstream processing and ladder detection. Downstream processing includes multiplexing and other chemistries including those involved in chemiluminescence. Detection can be of radioactive, fluorescent, or chemiluminescent-developed ladders or ladder probes. Downstream processing means chemical or other manipulation of sequence ladders either at the electrophoresis device 1 or at separate devices designed to accommodate the easily portable drum 13.

OTHER USES OF THE INSTANT INVENTION

The components of this invention, either as an integrated entity or individually, can be used productively for other applications besides DNA sequencing. For example, DNA fingerprinting with specific probes could be accomplished with increased throughput and resolution, and decreased electrophoresis time using a ribbon channeled plate drum electrophoresis device 1 and downstream processing and detection.

OTHER EMBODIMENTS

While a preferred embodiment of the instant invention has been illustrated and described, it will be apparent to those skilled in the art that many changes and modifications may be made without departing from the invention in its broader aspects. The appended claims are therefore intended to cover such changes and modifications as fall within the true spirit and scope of the invention.

We claim:

1. An apparatus for the sequencing of a DNA sample comprising:
    (a) a gel support unit having
        (1) an upper buffer chamber having an access slot, said upper buffer chamber mounted on,
        (2) a plate assembly having cover plate and ribbon channel plate defining a plurality of sample loading spaces wherein each sample loading space is open to said access slot and adjacent to a polymerized gel within the ribbon channel plate, said plate assembly further having an interface edge placed adjacent to;
    (b) a drum assembly having
        (1) a drum with a deposition membrane mounted adjacent to and spaced apart from said interface edge, defining a plate-drum gap,
        (2) a lower buffer chamber with a drum support unit, said drum placed upon said drum support unit and extending into said lower buffer chamber;
    (c) an electrical circuit having
        (1) an upper electrode mounted within said upper buffer chamber, and attached to a high voltage power supply,
        (2) a lower electrode mounted within said lower buffer chamber and attached to said high voltage power supply, and
        (3) a buffer solution(s) within said upper buffer chamber and said lower buffer chamber wherein a circuit is formed between said upper electrode and said lower electrode through said buffer solution in said upper buffer chamber, through said sample loading spaces, through said polymerized gel, and through a plate-drum interface defined in said plate-drum gap with said buffer solution from said lower buffer chamber, through buffer solution coating said deposition membrane, through the buffer solution within the lower buffer chamber to said lower electrode, and thence back to said power source;
    wherein when said DNA sample is placed in the sample receiving wells it is electrophoretically separated in temporal distribution along said deposition membrane surface.

2. The apparatus in claim 1 wherein said channel plate has a plurality of channels in an upper surface.

3. The apparatus in claim 1 wherein said plate assembly further comprises a temperature control plate mounted in contact with said ribbon channel plate.

4. The apparatus in claim 3 wherein said temperature control plate contains a plurality of baffle chambers, each of said baffle chambers being individually thermostated.

5. The apparatus in claim 3 wherein said temperature control plate, further comprises:
   an upper and lower surface;
   said upper surface being in contact with said ribbon channel plate;
   said lower surface being in contact with an upper platform.

6. The apparatus in claim 5 wherein said cover plate has a sample deposition slot disposed in alignment with said sample receiving wells.

7. The apparatus in claim 1 wherein said drum assembly further comprises a rotating means having a drive motor, sprocket, and chain assembly.

8. The apparatus in claim 1 wherein said first buffer solution and said second buffer solution are of the same composition.

9. The apparatus in claim 1 wherein said deposition membrane is selected from the group of charged nylon, uncharged nylon, and nitrocellulose.

10. The apparatus in claim 1 wherein a buffer absorbent underlayment is interdisposed between said drum surface and said deposition membrane.

11. The apparatus in claim 1 wherein the rotation of said drum is controlled by a computer.

12. The apparatus in claim 1 wherein the plate assembly is vertically disposed.

13. The apparatus in claim 1 wherein the plate assembly is horizontally disposed.

14. The apparatus in claim 1 wherein said apparatus further comprises process devices selected from the group of detection, chemical treatment, illumination, drying, or transfer of the deposition membrane.

15. A method for sequencing DNA samples, comprising the steps of:
   (a) providing a gel support unit having
      (1) an upper buffer chamber having an access slot, said upper buffer chamber mounted on,
      (2) a plate assembly having cover plate and ribbon channel plate defining a plurality of sample loading spaces wherein each sample loading space is open to said access slot and adjacent to a polymerized gel within the ribbon channel plate, said plate assembly further having an interface edge;
   (b) placing a drum assembly adjacent to said gel said interface edge, said drum assembly having
      (1) a drum with a deposition membrane mounted adjacent to and spaced apart from said interface edge, defining a plate-drum gap,
      (2) a lower buffer chamber with a drum support unit, said drum placed upon said drum support unit and extending into said lower buffer chamber;
   (c) providing electrical circuit having
      (1) an upper electrode mounted within said upper buffer chamber, and attached to a high voltage power supply, and
      (2) a lower electrode mounted within said lower buffer chamber and attached to said high voltage power supply,
   (d) filling said sample spaces with said DNA samples;
   (e) filling said upper buffer chamber and said lower buffer chamber with at least one buffer solution;
   (f) rotating said drum and forming a plate-drum interface in said plate-drum gap with said buffer solution from said lower buffer chamber;
   (g) imposing an electrical potential across the upper electrode and the lower electrode and passing electrical current between said upper electrode and said lower electrode through said buffer solution in said upper buffer chamber, through said DNA sample, through said polymerized gel, and through buffer solution coating said deposition membrane, through the buffer solution within the lower buffer chamber to said lower electrode, and thence back to said power source; and
   (h) electrophoretically separating said DNA sample in temporal distribution on said deposition membrane.

16. The method as recited in claim 15, wherein there are at least 48 sample spaces.

* * * * *